(12) United States Patent
Shuchman et al.

(10) Patent No.: US 11,169,085 B2
(45) Date of Patent: Nov. 9, 2021

(54) HANDHELD SPECTRORADIOMETER SYSTEM, COMPUTER-READABLE MEDIA, AND CALIBRATION METHODS

(71) Applicant: MICHIGAN TECHNOLOGICAL UNIVERSITY, Houghton, MI (US)

(72) Inventors: Robert Shuchman, Houghton, MI (US); Michael Sayers, Houghton, MI (US); Reid Sawtell, Houghton, MI (US); Karl Bosse, Houghton, MI (US)

(73) Assignee: MICHIGAN TECHNOLOGICAL UNIVERSITY, Houghton, MI (US)

( * ) Notice: Subject to any disclaimer, the term of this patent is extended or adjusted under 35 U.S.C. 154(b) by 39 days.

(21) Appl. No.: 16/793,350

(22) Filed: Feb. 18, 2020

(65) Prior Publication Data

US 2020/0264095 A1 Aug. 20, 2020

Related U.S. Application Data

(60) Provisional application No. 62/808,121, filed on Feb. 20, 2019.

(51) Int. Cl.
*G01J 3/28* (2006.01)
*G01N 21/27* (2006.01)
*G01N 33/18* (2006.01)
*G01N 21/25* (2006.01)

(52) U.S. Cl.
CPC ......... *G01N 21/274* (2013.01); *G01N 21/255* (2013.01); *G01N 33/1826* (2013.01); *G01N 2201/0221* (2013.01); *G01N 2201/127* (2013.01)

(58) Field of Classification Search
CPC ............. G01N 21/274; G01N 33/1826; G01N 21/255; G01N 2201/0221; G01N 2201/127; G01N 21/03; G01J 3/0272; G01J 2003/2866; G01J 3/28
See application file for complete search history.

(56) References Cited

U.S. PATENT DOCUMENTS

2002/0012461 A1* 1/2002 MacKinnon ......... H04N 1/6088
382/164
2018/0306827 A1* 10/2018 Pierce, III ............ G01N 33/948

* cited by examiner

*Primary Examiner* — Abdullahi Nur
(74) *Attorney, Agent, or Firm* — Michael Best & Friedrich LLP (57) ABSTRACT

Non-transitory computer-readable media, spectroradiometer systems, and methods for calibrating a spectroradiometer. In one embodiment, a non-transitory computer-readable medium includes instructions that, when executed by an electronic processor, cause the electronic processor to perform a set of operations. The set of operations includes receiving spectral data regarding an object-of-interest that is captured by a handheld spectroradiometer, detecting a characteristic of the object-of-interest by performing a spectral analysis on the spectral data that is received, and controlling a display to display the characteristic of the object-of-interest.

23 Claims, 3 Drawing Sheets

HANDHELD SPECTRORADIOMETER SYSTEM, COMPUTER-READABLE MEDIA, AND CALIBRATION METHODS

CROSS-REFERENCE TO RELATED APPLICATION

This application claims priority to and benefit of U.S. Provisional Application No. 62/808,121, filed on Feb. 20, 2019, the entire content of which is incorporated herein by reference.

FIELD

Embodiments of the present disclosure generally relate to spectroradiometers, and more particularly, relate to detection of a characteristic of an object-of-interest by spectral analysis of spectral data captured by a handheld spectroradiometer.

BACKGROUND

Conventional spectroradiometers are used to detect spectral data of harmful algae blooms (referred to herein as "HABs") that contain toxins. Of particular concern is the documentation that HABs have been increasing worldwide in both intensity and geographic distribution in the past few decades. Moreover, this increase in HABs occurrence and extent has also been noted in the Great Lakes basin. Thus, the ability to detect, monitor and assess HABs in the Great Lakes basin is important to those living in this region.

In freshwater environments, HABs are most commonly associated with one algal group, cyanobacteria or blue-green algae. Colonial cyanobacteria blooms commonly occur in many eutrophic regions throughout the world. Many cyanobacteria produce toxins and toxin concentrations in cyanobacteria blooms (referred to herein as "cyanoHAB") may have serious potential negative impacts on aquatic resources, public health, and community economics.

There are two unique traits of cyanoHABs. The first important trait is the presence of phycobilin pigments in all cyanobacteria. Because these pigments are one of the dominant light absorbing pigments in cyanobacteria and these pigments are not found in abundance in other algal groups, they have been used to detect and monitor cyanobacteria using a variety of sensing techniques. The ability to discriminate cyanobacteria blooms from other algal blooms in freshwater has been strongly dependent on an ability to determine phycocyanin concentrations. For remote sensing applications in the Great Lakes, conventional techniques use the Fluorescence Line Height (FLH) algorithm that exploits the spectral shape of cyanobacteria absorption features in the red and "red edge" portions of the electromagnetic spectrum to quantify cyanobacteria blooms in the western basin of Lake Erie. Additionally, other conventional techniques define a relationship between surface chlorophyll and phycocyanin concentrations in Lake Erie for monitoring HAB trends.

The second important trait of many cyanoHABs is the formation of surface scums via the production of cellular vacuoles. Surface scums are particularly troublesome as they are associated with high densities of cyanobacteria and have been linked to very high concentrations of toxins. Moreover, health organizations have used the presence of scums as an indicator of high toxin concentrations and an important health signal. Toxin concentrations in surface scum may be one hundred times the toxin concentrations in the water below.

However, conventional spectroradiometers are expensive and require an expert with extensive training in the field of remote sensing of HABs to generate accurate spectral data regarding HABs. What is needed is an inexpensive spectroradiometer that requires little to no training to generate accurate spectral data and derived information regarding a number of different applications including, but not limited to, a HAB application.

SUMMARY

A non-transitory computer-readable medium and a spectroradiometer system of the present disclosure addresses the deficiencies of the conventional spectroradiometers. For example, the spectroradiometer system of the present disclosure includes a handheld spectroradiometer communicatively connected to a mobile computing device, which are significantly less expensive (two to ten times less expensive) than conventional spectroradiometers and require little to no training to generate accurate spectral data that is on par with the conventional spectroradiometers. A number of comparisons between the described low cost handheld spectroradiometer and a conventional spectroradiometer revealed the differences between the spectra are negligible in respect to the uncertainty inherent in the algorithms used to generate the derived water quality products. In one example, the spectroradiometer system of the present disclosure generates accurate spectral data by observing the radiance values in the blue, green, red and infrared parts of the electromagnetic spectrum to estimate phycocyanin and the surface scum index of HABs. However, the spectroradiometer system of the present disclosure may also generate accurate spectral data in numerous other applications as described in greater detail below. A significant improvement over conventional spectroradiometers is the flexibility of using the spectroradiometer system of the present disclosure in different application while requiring minimal training to generate accurate results.

In one embodiment, the present disclosure includes a non-transitory computer-readable medium comprising instructions that, when executed by an electronic processor, cause the electronic processor to perform a set of operations. The set of operations includes receiving spectral data regarding an object-of-interest that is captured by a handheld spectroradiometer, detecting a characteristic of the object-of-interest by performing a spectral analysis on the spectral data that is received, and controlling a display to display the characteristic of the object-of-interest.

In another embodiment, the present disclosure includes a spectroradiometer system. The spectroradiometer system includes a mobile computing device and a handheld spectroradiometer. The mobile computing device includes a memory, a communication interface, and an electronic processor communicatively connected to the memory and the communication interface. The electronic processor is configured to receive spectral data regarding an object-of-interest, and detect a characteristic of the object-of-interest by performing a spectral analysis on the spectral data that is received. The handheld spectroradiometer includes an image sensor with a diffraction device, a memory, a communication interface, and an electronic processor communicatively connected to the memory, the communication interface, and the image sensor with the diffraction device. The electronic processor configured to control the image sensor to capture the spectral data regarding the object-of-interest based on reflected light from the object-of-interest.

In yet another embodiment the invention provides a method of calibrating a spectroradiometer. The method includes mapping each pixel in a calibration image to a wavelength, averaging spectra of the each pixel in the calibration image together, determining a correction factor by comparing the spectra that is averaged together to reference spectra, and regularizing spectra by applying the correction factor that is determined to spectra in a non-calibration image.

Other aspects of the present disclosure will become apparent by consideration of the detailed description and accompanying drawings.

DETAILED DESCRIPTION

Before any embodiments of the present disclosure are explained in detail, it is to be understood that the present disclosure is not limited in its application to the details of construction and the arrangement of components set forth in the following description or illustrated in the following drawings. The present disclosure is capable of other embodiments and of being practiced or of being carried out in various ways.

The present disclosure includes, among other things, a system including a mobile computing device (e.g., a smartphone, tablet, laptop, or other suitable mobile computing device) and a light diffraction device (e.g., a spectroradiometer attachment or other suitable light diffraction device) to monitor some of the key characteristics of cyanoHABs described above. Modern smartphones are equipped with cameras of sufficient sensitivity to record spectral information of varying trophic state of inland lakes and other water bodies. However, out-of-the-box smartphone cameras do not provide the spectral information (i.e. number of electromagnetic spectrum wavelengths) to accurately determine algal abundance. A system of the present disclosure records very detailed spectral information. Thus, the system of the present disclosure in conjunction with custom phone or other mobile computing device-based processing software produces accurate spectral information for the determination of algal abundance and presence/absence of potentially harmful algae in natural waters.

The spectral data generated by the system of the present disclosure provides methods for determining chlorophyll concentrations, phycocyanin concentrations and surface algal scums in order to discriminate cyanobacteria blooms from other algal blooms and to predict potential public health risks. This system will also provide operators the ability to detect, monitor, and assess cyanoHABs in any body of water. It should be emphasized that this system will also provide very rapid and simple screening (i.e., screening within minutes instead of days) of potentially harmful algae in any water body. Moreover, the development of these new products will allow for examining the relationship of phycocyanin concentrations and surface scums to toxin levels. It should be noted this smartphone-based system (set of algorithms) can be used by a variety of remote sensing platforms including shipborne, UAVs, aircraft, and high resolution satellites.

Figure 1:
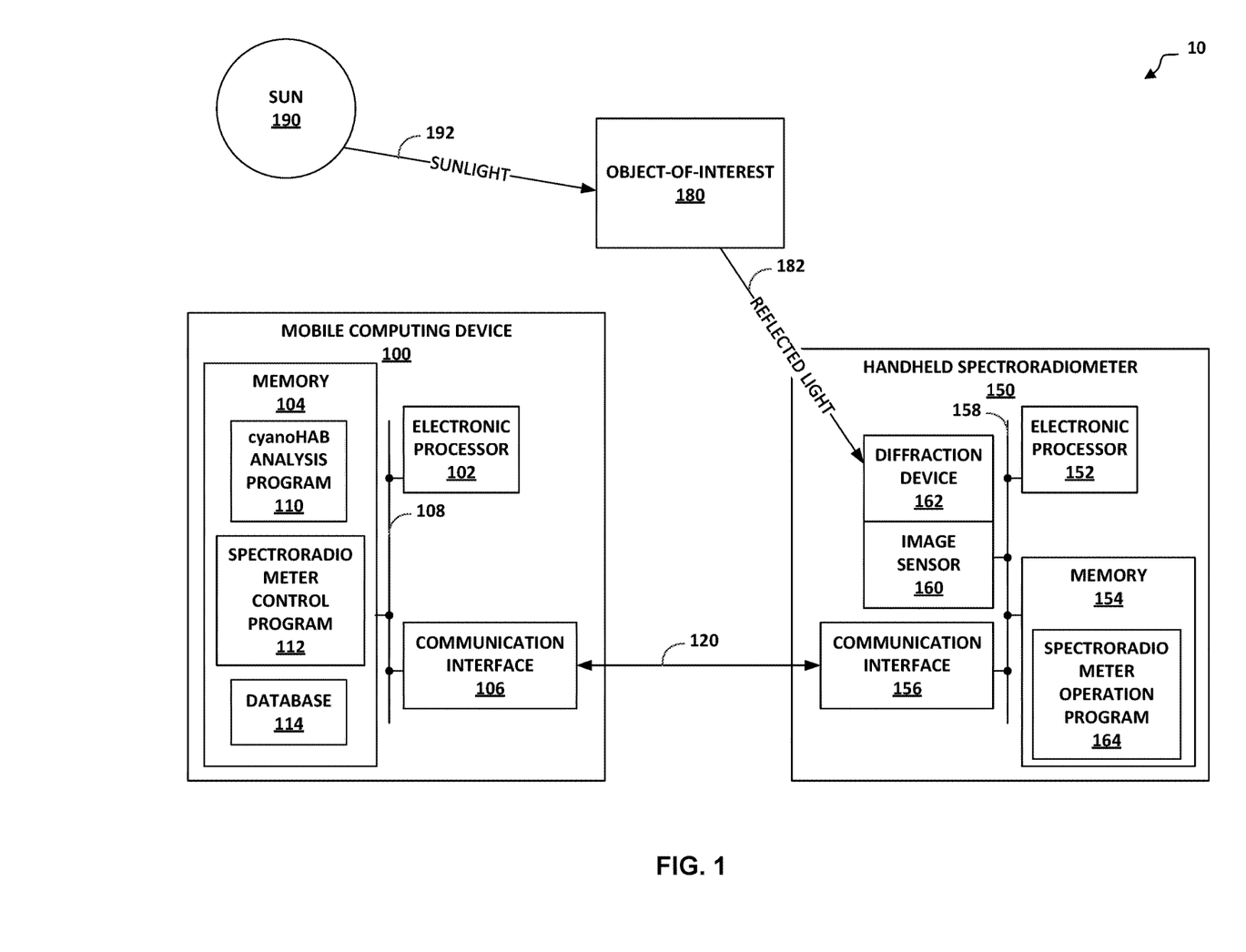
FIG. 1 is a block diagram of an example spectroradiometer system according to various aspects of the present disclosure.

FIG. 1 is a block diagram of an example spectroradiometer system 10 according to various aspects of the present disclosure. In the example of FIG. 1, the spectroradiometer system 10 includes a mobile computing device 100, a handheld spectroradiometer 150, an object of interest 180, and the Sun 190. As illustrated in FIG. 1, the Sun 190 illuminates the object-of-interest 180 with sunlight 190 at a specific angle, which is reflected off of the object-of-interest 180 as reflected light 182. The reflected light 182 is reflected from the object-of-interest 180 to the handheld spectroradiometer 150. The handheld spectroradiometer 150 communicates data based on the reflected light 182 to the mobile computing device 100 over the communication link 120. As explained above, in some examples, the mobile computing device 100 is a smartphone, a tablet, or a computer. In other examples, the mobile computing device 100 may be a shipborne control system, a UAV control system, an aircraft control system, a high resolution satellite control system, or other suitable control system. Additionally, in some examples, the communication link 120 may be a wireless communication link or a wired communication link.

The mobile computing device 100 includes an electronic processor 102, a memory 104, a communication interface 106 that may communicate over one or more buses (e.g., a communication bus 108). In some examples, the electronic processor 102 is implemented as a microprocessor with separate memory, such as the memory 104. In other embodiments, the electronic processor 102 may be implemented as a microcontroller (for example, with the memory 104 on the same chip). In other embodiments, the electronic processor 102 may be implemented using multiple processors. In addition, the electronic processor 102 may be implemented partially or entirely as, for example, a field-programmable gate array (FPGA), an application specific integrated circuit (ASIC), or other suitable processing device. In this instance, the memory 104 may not be needed or may be modified accordingly.

Figure 3:
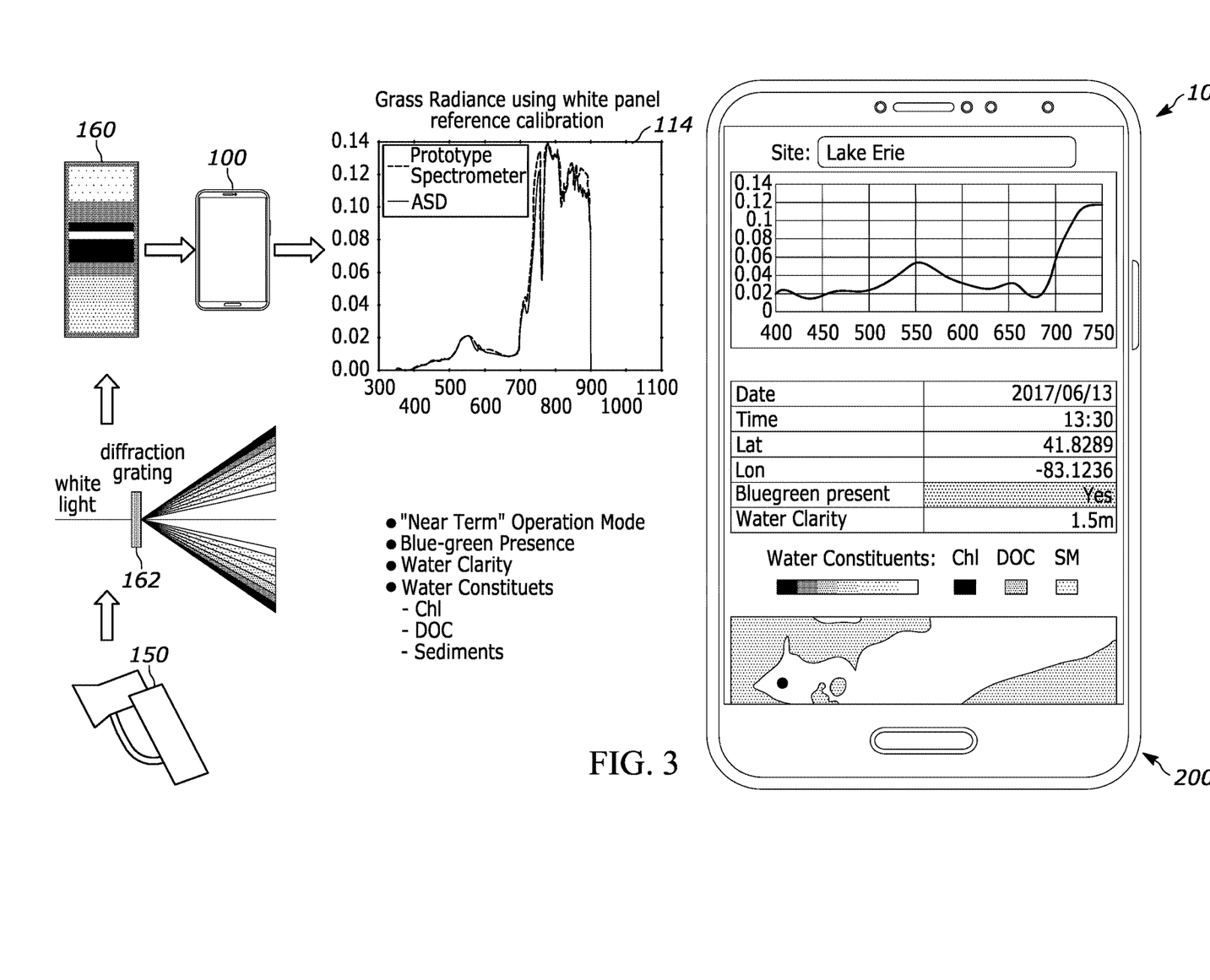
FIG. 3 is a conceptual diagram of the example spectroradiometer system according to various aspects of the present disclosure.

In some examples, the mobile computing device 100 may also include a display (not shown in FIG. 1). For example, when the mobile computing device 100 is a smartphone 100, the smartphone 100 displays a graphical user interface (e.g., the graphical user interface 200 as illustrated in FIG. 3).

The memory 104 includes non-transitory, computer-readable memory that stores instructions that are received and executed by the electronic processor 102 to carry out functionality of the mobile computing device 100 described herein. The memory 104 may include, for example, a program storage area and a data storage area. The program storage area and the data storage area may include combinations of different types of memory, such as read-only memory and random-access memory.

The communication interface 106 enables wireless communication from the mobile computing device 100 to, for example, the handheld spectroradiometer 150 over the communication link 120. In other examples, rather than wireless communication, the communication interface 106 may include wired communication components, for example, a network interface for a wired connection as the communication link 120 to the handheld spectroradiometer 150.

As illustrated in FIG. 1, the memory 104 includes a cyanoHAB analysis program 110, a spectroradiometer control program 112, and a database 114. The cyanoHAB analysis program 110 is a program for determining chlorophyll concentrations, phycocyanin concentrations, and surface algal scums based on spectral data in order to discriminate cyanobacteria blooms from other algal blooms. The spectroradiometer control program 112 is a program for communicating and controlling the handheld spectroradiometer 150. The spectroradiometer control program 112, when executed by the electronic processor 102, controls the handheld spectroradiometer 150 to perform the control operations as described below. The database 114 stores the data received from the handheld spectroradiometer 150 over the communication link 120.

The handheld spectroradiometer 150 includes an electronic processor 152, a memory 154, a communication interface 156, a communication bus 158, an image sensor 160, and a diffraction device 162 that may communicate over one or more buses (e.g., a communication bus 158). In some examples, the electronic processor 152 is implemented as a microprocessor with separate memory, such as the memory 154. In other embodiments, the electronic processor 152 may be implemented as a microcontroller (for example, with the memory 154 on the same chip). In other embodiments, the electronic processor 152 may be implemented using multiple processors. In addition, the electronic processor 152 may be implemented partially or entirely as, for example, a field-programmable gate array (FPGA), an application specific integrated circuit (ASIC), or other suitable processing device. In this instance, the memory 104 may not be needed or may be modified accordingly.

Further, while the handheld spectroradiometer 150 uses the term "handheld," this term does not limit the spectroradiometer 150 to only being held in the hand of a user. Instead, the use of "handheld" is intended to be considered "mobile," where the handheld spectroradiometer 150 may be mounted to the mobile computing device 100 as described above or held in the hand of a user.

The memory 154 includes non-transitory, computer-readable memory that stores instructions that are received and executed by the electronic processor 152 to carry out functionality of the handheld spectroradiometer 150 described herein. The memory 154 may include, for example, a program storage area and a data storage area. The program storage area and the data storage area may include combinations of different types of memory, such as read-only memory and random-access memory.

The communication interface 156 enables wireless communication from the handheld spectroradiometer 150 to, for example, the mobile computing device 100 over the communication link 120. In other examples, rather than wireless communication, the communication interface 156 may include wired communication components, for example, a network interface for a wired connection as the communication link 120 to the mobile computing device 100.

The image sensor 160 is any suitable image sensor. For example, the image sensor 160 may be a Raspberry PiCamera NOIR V2 camera which incorporates the Sony IMX219 8-megapixel image sensor. The diffraction device 162 may be a thin slit device that allows the reflected light 182 to enter the diffraction device 162, where the reflected light strikes a diffraction gradient that creates a separation of wavelengths (referred to herein as a "blaze") when observed from a specific angle.

The image sensor 160 is mounted at the specific angle to view and capture the blaze as an image. The image capture result is a two dimensional image where each column in the image roughly corresponds to the spectral signature of light entering the diffraction device 162 at the intersection of the column and the optical slit. Each row of the blaze corresponds to a particular spectral mixture of light governed by the properties of the diffraction gradient.

As illustrated in FIG. 1, the memory 154 includes a spectroradiometer operation program 164. The spectroradiometer operation program 164 is a program for operating as well as calibrating the handheld spectroradiometer 150. The spectroradiometer operation program 164, when executed by the electronic processor 152, controls the handheld spectroradiometer 150 to perform the control operations as described below. The memory 154 stores (e.g., temporarily or permanently) the data received from the image sensor 160 before transmitting the data over the communication link 120 to the mobile computing device 100.

The cyanoHAB analysis program 110 is a program that utilizes the calibrated spectra received from the spectroradiometer operation program 164 to generate derived products (including but not limited to presence of blue-green algae, water clarity, and concentrations of water constituents such as chlorophyll, dissolved organic carbon, and suspended minerals). These products are typically the output of algorithms developed and verified by the remote sensing scientific community. This program is modular and new algorithms can easily be added or removed to target different applications.

The spectroradiometer control program 112 is a program that guides the user through the process of collecting quality spectra. It combines orientation sensors on either the mobile computing device 100 or the handheld spectroradiometer 150 with the calculated solar zenith angle and azimuth based on location and time of day to guide the user to aim the handheld spectroradiometer at the object of interest at the optimal viewing orientation. When the program has verified the user has followed the guidance, it initiates the spectroradiometer operation program 164.

The spectroradiometer operation program 164 is a program that causes the electronic processor 152 to interface with the image sensor 160 to determine the optimal integration time, capture an image, process the image into a spectral response using calibration parameters, and returns the data to the mobile computing device 100. As described below in FIG. 2, the spectroradiometer operation program 164 when executed by electronic processor 152 may also calibrate the spectroradiometer system 10. However, in other examples, the spectroradiometer control program 112 executed by the electronic processor 102 may also control the handheld spectroradiometer to perform the calibration method described below and illustrated in FIG. 2.

The spectroradiometer system 10 may be used in several different applications including water quality assessment, invasive species identification, vegetation health, crop stress/blight detection, mineral prospecting, road surface assessment, etc. The spectroradiometer system 10 may also have one or more operational modes. For example, the spectroradiometer system 10 may have a self-contained mode, a web-connected mode, or both. In the self-contained mode, the mobile computing device 100 process and records data and provides information to a user without being connected to the Internet. In the web-connected mode, the mobile computing device 100 may access the cloud, process data and record the data to the cloud for crowd-sourcing of data, and provide spectral information to a user that may be based at least in part on information from the cloud.

The handheld spectroradiometer 150 relies on a set of algorithms and procedures (and are part of spectroradiometer operation program 164) to generate high quality hyperspectral data from a device constructed from off-the-shelf electronics and a 3D printed housing. The off-the-shelf nature of the device's construction inevitably results in imprecision in the spectral output because misalignment and minor differences in the parts combine to create distortions that are unique to each device. A calibration method as described below compensates for these unique distortions in each device.

Figure 2:
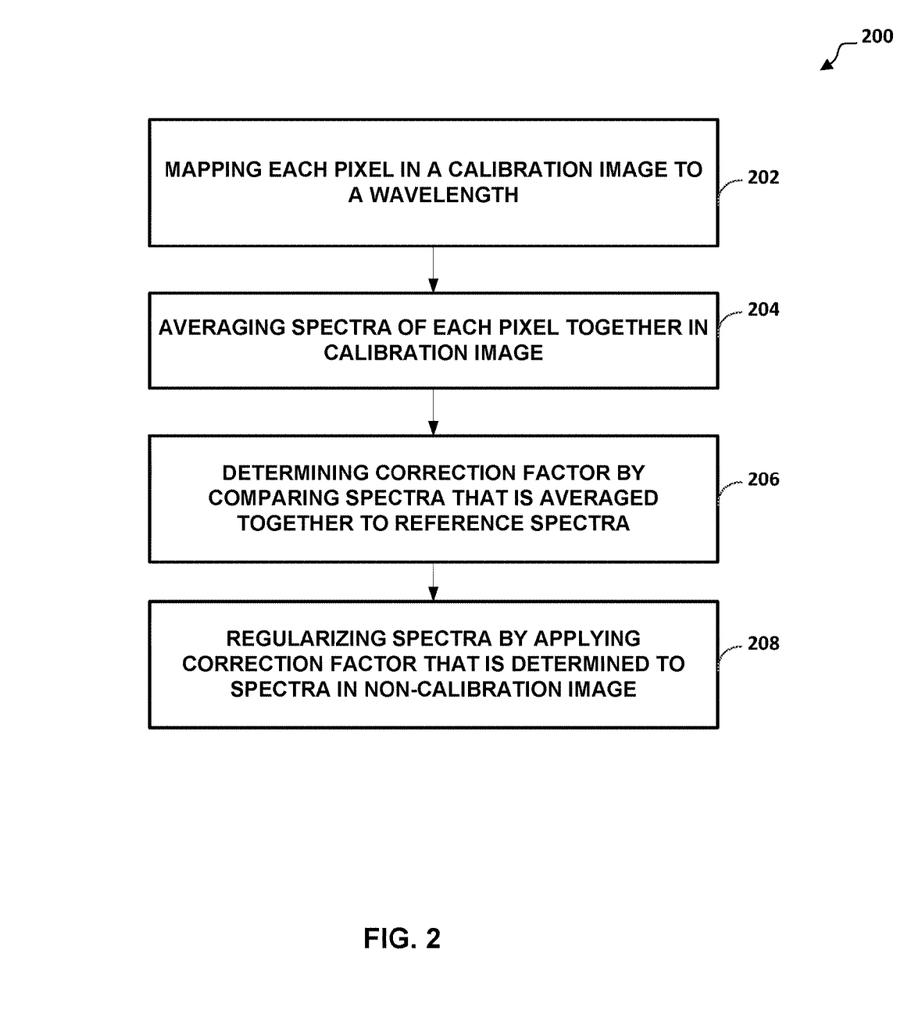
FIG. 2 is a flowchart illustrating a method for calibrating a handheld spectroradiometer, according to various aspects of the present disclosure.

FIG. 2 is a flowchart illustrating a method 200 for calibrating a handheld spectroradiometer. The method 200 includes mapping each pixel in a calibration image to a wavelength (block 202). For example, the electronic processor 152 maps each pixel in a calibration image generated by the image sensor 160 to a wavelength.

The method 200 includes averaging spectra of each pixel together in the calibration image (block 204). For example, the electronic processor 152 averages spectra of each pixel together in the calibration image generated by the image sensor 160.

The method 200 includes determining a correction factor by comparing the spectra that is averaged together to a reference spectra (block 206). For example, the electronic processor 152 determines a dark pixel value and calibration coefficients by comparing the spectra that is averaged to a reference spectra that is generated by an ASD FieldSpec unit.

The method 200 also includes regularizing spectra in a non-calibration image based on the correction factor that is determined (block 208). For example, the electronic processor 152 regularizes spectra by applying the correction factor that is determined to spectra in a non-calibration image from the image sensor 160.

Specifically, at block 202, wavelength mapping begins with the theory of how optical slits, diffraction gradients, and camera's interact to create an image with a separation of wavelengths. A model has been developed to convert the approximate known parameters of the device construction to what the camera should theoretically view. Model inputs include distance between diffraction gradient and optical slit, vertical height between the camera aperture and the diffraction gradient, horizontal distance from the camera aperture to center of the diffraction gradient (over which the optical slit is assumed to be centered), viewing angle of the camera, angle between the camera's center look direction and the diffraction gradient, width of the slit, and resolution of the camera. With this information the model computes the theoretic wavelengths the center column of the camera should observe. This provides a good initial estimate, but due to device imprecision it is not sufficient alone to generate high quality spectra: the observed wavelengths on the device are stretched and distorted and if not compensated for will result in significant deviations (10-30 nanometers (nm) misalignment per pixel is typical), these distortion are also device specific: corrections for one device are unlikely to work well for another.

To compensate for device specific distortions, some form or reference must be introduced that will provide an indication of what the real measured wavelength is. Fortunately, a reference signal is widely available: sunlight. The solar irradiance spectrum is rich with a variety of wavelength specific spectral features known as Fraunhofer lines, some of which are significant enough to be easily recognized even under heavy distortion, this is important because wavelength alignment happens prior to calibration, so the incoming signal is modulated by the sensor response characteristics. The camera sensor incorporates a Bayer filter, an alternating Blue, Green, Green, Red checkerboard pattern that allows the camera to generate red-green-blue (RGB) images. In our case this filter is undesirable as the filter reduces the spectral bandwidth viewable by each pixel, interposing its response characteristics (which also deviate slightly from device to device from published values) on top of an unknown spectra. The recognizable features in the solar irradiance spectrum are critical to overcoming this, as the solar irradiance allows for specific points in the image to be related to known wavelengths for each column in the image. This is achieved by combining the AM 1.5 Reference Spectrum (http://rredc.nrel.gov/solar/spect ra/am1.5/) with the published RGB response values of the IMX219 sensor to generate a set of reference spectra for the G, b, and A Fraunhofer lines as they should appear on the device. The theoretic wavelengths derived from the diffraction gradient model are used to constrain the search area, and cross correlation combined with known relationships between Fraunhofer line positions and the camera response is used to determine the best match location for that feature in the observed spectra. Of the three lines, the G and A are very reliable while the b line is less reliable. It is possible to match additional features, but the additional features are less reliable than the b line and generally do not contribute much as the additional features are frequently masked by the distortion introduced by the RGB filters, which restricts this technique to only a crude fit of the actual wavelengths. It does however give solid tie points on both ends of the spectrum and creates a good estimate of the valid viewing region within the image (the left and right sides of the image typically view the interior of the spectroradiometer and are not useful for generating spectra). To account for individual column error, the X and Y positions of the tie points for each Fraunhofer line are used to generate a 2nd order polynomial fit which is subsequently used to model tie point locations for each column.

The next step of the calibration procedure strives to model the difference between real and theoretic wavelengths as observed by the device on a per column basis. Using the tie points generated in the previous polynomial fits, a non-linear optimization is run using the initial camera parameters fed into the diffraction gradient model, attempting to tune the input model parameters to generate a better fit. Using a dual approach, both the wavelength alignment generated by the initial and optimized model parameters are fed into a second non-linear optimization that attempts to generate another 2nd order polynomial modeling the offset between the gradient of the observed signal and the theoretic signal as predicted by the reference spectrum and published response values. The residual is computed as the sum of the gradient differences per wavelength to a fractional power (typically close to 0.5). The motivation of using the image gradient is that the image gradient will tend to focus on aligning spectral features rather than the slopes of the camera spectral response. Those slopes are still present in the gradient though, which is the motivation behind the fraction power rather than the typical sum of squares approach: a fractional power increases the relative fitting power of the many smaller features in comparison to the single massive shape of the spectral response. The results of this optimization procedure are tracked, and finally the best combination of column and use of initial or optimized model parameters is selected to generate a reference wavelength alignment for that column. What remains then is to model the distortion every other column experiences relative to the reference column, which generates a mapping between them.

Distortion mapping is based on the assumption that the distortions are smooth curves across the image from left to right, but change in severity up and down the image. To map these, each set of wavelengths is pulled from the Bayer image into an image of a single color. Noise reduction filters are applied, each column is normalized to the largest value in that column, and then the vertical gradient is computed. This smoothed, normalized vertical gradient is then used as input to a contour finding routine. The contour finding routing is fed a list of local maximums and minimums in the gradient image, which it then attempts to fit. The result is a large set of contours which may or may not accurately model the distortion in the image and must be filtered. Contour filtered uses the left to right assumption, specifying that only contours that consistently advance across the image are selected. Each remaining contour then has a 2nd order polynomial fit calculated for it, and these fitting equations are then further filtered by eliminating fits that significantly deviate from the contour that generated it. The result is a set of equations that smoothly model the image distortion at a variety of vertical positions spanning the observable spectral range. Then, for each column, the points produced by the array or polynomial fits is then used to compute another 2nd order fit for that column that models the mapping from the reference column to the sample column. The fit in this case is weighted to preferentially target the G and A Fraunhofer line fits previously generated in the analysis since these are the most reliable features. Once this is completed, the result is a mapping of every pixel in the image to the reference column, which can then be translated into a per-pixel wavelength map.

The resulting mapping of pixel to wavelength, when displayed on a scatter plot, demonstrates a significant amount of signal noise due to imperfections in the device construction, particularly due to variations in the optical slit width across the image (even small variations, such as a speck of dust, can result in large magnitude changes). To account for this, with respect to block 204, the pixels sharing like wavelength values are averaged together. The averaging procedure used, in one example, begins by binning each pixel, bins are calculated from 380-900 nm, with 0.5 nm width. For example, the first bin would include all pixels labeled between 379.75 and 380.25, followed by 380.25-380.75, 380.75-381.25, and so on. The bin mapping is saved to the handheld device to be used in all future signal calculations. That final signal is computed using a weighted averaging with a Gaussian kernel of width 5, sigma 1.5. The result is a consistent, smooth signal that can be used to determine the calibration response coefficients, and have those same coefficients applied in the future to produce useable spectra.

With respect to block 206, the handheld spectroradiometer to be calibrated is pointed into an integrating sphere, a set of images is captured using different integration times, and a reference spectra is generated by observing the sphere with a highly-calibrated device (e.g., an ASD FieldSpec™ device) that is used to determine the 'true' signal. The handheld spectra at different integration times are used with a simple linear fit to calculate the intercept value, which represents the dark pixel contribution and is subtracted from the observed spectra. The reference spectra is then divided by the dark pixel corrected handheld spectra, generating a set of correction coefficients. The dark pixel value and calibration coefficients are then saved to the device as a correction factor.

Lastly, with respect to block 208, the handheld spectroradiometer regularizes spectra by applying the correction factor to spectra in non-calibration images, which generates a spectra that has a quality that is similar to a quality of spectra generated by a highly-calibrated device (e.g., the ASD FieldSpec™ device). For example, the electronic processor 152 may apply the correction factor to spectra from non-calibration images to generate spectra data that is comparable to a conventional spectroradiometer that costs anywhere from two to ten times more than the cost of the handheld spectroradiometer 150.

FIG. 3 is a conceptual diagram of the example spectroradiometer system 10 according to various aspects of the present disclosure. FIG. 3 summarizes the end-to-end system 10. The handheld spectroradiometer 150 is aimed at a given target of interest. The example graphical user interface 300 will guide the user to collect spectra at an optimized viewing geometry and initiate the spectra collection process on the handheld spectroradiometer 150. Light from the target passes through the diffraction gradient 162 which is then captured by the image sensor 160. The resulting data is processed by the handheld spectroradiometer 150 and communicated over the communication link 120 to the mobile computing device 100. The processed spectra can then be displayed alongside data stored in the database 114 for comparison. The example graphical user interface 300 displays the collected spectra as well as the derived products (including, but not limited to, presence of blue-green algae, water clarity, and concentrations of water constituents such as chlorophyll, dissolved organic carbon, and suspended minerals) from the cyanoHAB analysis program 110 and ancillary data which may include latitude, longitude, date, time of collection and photo of the target. This end-to-end process takes a few minutes at most for a non-expert in contrast to existing systems that typically require a trained professional a few hours or more to produce similar results.

The following are enumerated examples of the non-transitory computer-readable media, spectroradiometer systems, and methods of the present disclosure:

Example 1

A non-transitory computer-readable medium comprising instructions that, when executed by an electronic processor, cause the electronic processor to perform a set of operations comprising: receiving spectral data regarding an object-of-interest that is captured by a handheld spectroradiometer; detecting a characteristic of the object-of-interest by performing a spectral analysis on the spectral data that is received; and controlling a display to display the characteristic of the object-of-interest.

Example 2

The non-transitory computer-readable medium of Example 1, wherein the set of operations further includes mapping each pixel in a calibration image to a wavelength; averaging spectra of the each pixel in the calibration image together; determining a correction factor by comparing the spectra that is averaged together to reference spectra; and regularizing the spectral data regarding the object-of-interest by applying the correction factor that is determined.

Example 3

The non-transitory computer-readable medium of Examples 1 or 2, wherein the set of operations further includes retrieving the calibration image and the reference spectra from a memory; and controlling a handheld spectroradiometer to transmit the spectral data regarding the object-of-interest.

Example 4

The non-transitory computer-readable medium of any of Examples 1-3, wherein receiving the spectral data regarding the object-of-interest further includes controlling an image sensor of handheld spectroradiometer to capture the spectral data regarding the object-of-interest, and wherein the set of operations further includes mapping each pixel in a calibration image to a wavelength; average spectra of the each pixel in the calibration image together; determine a correction factor by comparing the spectra that is averaged together to reference spectra; and regularize the spectral data regarding the object-of-interest by applying the correction factor that is determined.

Example 5

The non-transitory computer-readable medium of Example 4, wherein the set of operations further includes retrieving the calibration image and the reference spectra from a memory of a handheld spectroradiometer.

Example 6

The non-transitory computer-readable medium of any of Examples 1-5, wherein the object-of-interest is a body of water, and wherein the characteristic that is detected is one or more characteristics selected from a group consisting of: a presence of blue-green algae, a clarity of the body of water, a concentration of chlorophyll, a concentration of dissolved organic carbon, and a concentration of suspended minerals.

Example 7

A spectroradiometer system comprising: a mobile computing device including a memory, a communication interface, and an electronic processor communicatively connected to the memory and the communication interface, the electronic processor configured to receive spectral data regarding an object-of-interest, and detect a characteristic of the object-of-interest by performing a spectral analysis on the spectral data that is received; and a handheld spectroradiometer including an image sensor with a diffraction device, a memory, a communication interface, and an electronic processor communicatively connected to the memory, the communication interface, and the image sensor with the diffraction device, the electronic processor configured to control the image sensor to capture the spectral data regarding the object-of-interest based on reflected light from the object-of-interest.

Example 8

The spectroradiometer system of Example 7, wherein the electronic processor of the mobile computing device is further configured to map each pixel in a calibration image to a wavelength, average spectra of the each pixel in the calibration image together, determine a correction factor by comparing the spectra that is averaged together to reference spectra, and regularize the spectral data regarding the object-of-interest by applying the correction factor that is determined.

Example 9

The spectroradiometer system of Example 8, wherein the memory of the mobile computing device includes the calibration image and the reference spectra, and wherein the electronic processor of the mobile computing device is further configured to retrieve the calibration image and the reference spectra from the memory of the mobile computing device, and receive the spectral data regarding the object-of-interest from the handheld spectroradiometer.

Example 10

The spectroradiometer system of any of Examples 7-9, wherein the electronic processor of the handheld spectroradiometer is further configured to map each pixel in a calibration image to a wavelength, average spectra of the each pixel in the calibration image together, determine a correction factor by comparing the spectra that is averaged together to reference spectra, and regularize the spectral data regarding the object-of-interest by applying the correction factor that is determined.

Example 11

The spectroradiometer system of Example 10, wherein the memory of the handheld spectroradiometer includes the calibration image and the reference spectra, and wherein the electronic processor of the handheld spectroradiometer is further configured to retrieve the calibration image and the reference spectra from the memory of the handheld spectroradiometer.

Example 12

The spectroradiometer system of any of Examples 7-11, wherein the communication interface of the mobile computing device and the communication interface of the handheld spectroradiometer are configured to wirelessly communicate with each other.

Example 13

The spectroradiometer system of any of Examples 7-11, wherein the communication interface of the mobile computing device and the communication interface of the handheld spectroradiometer are configured to communicate with each other via a wired connection.

Example 14

The spectroradiometer system of any of Examples 7-13, wherein the object-of-interest is a body of water, and wherein the characteristic that is detected is one or more characteristics selected from a group consisting of: a presence of blue-green algae, a clarity of the body of water, a concentration of chlorophyll, a concentration of dissolved organic carbon, and a concentration of suspended minerals.

Example 15

The spectroradiometer system of any of Examples 7-14, wherein the handheld spectroradiometer is mounted to a housing structure of the mobile computing device, and wherein the mobile computing device is one selected from a group consisting of: a smartphone, a tablet, a computer, a shipborne control system, a UAV control system, an aircraft control system, and a high resolution satellite control system.

Example 16

A method for calibrating a spectroradiometer, the method comprising: mapping each pixel in a calibration image to a wavelength; averaging spectra of each pixel in the calibration image together; determining a correction factor by comparing the spectra that is averaged together to reference spectra; and regularizing spectra by applying the correction factor that is determined to spectra in a non-calibration image.

Example 17

The method of Example 16, further comprising: retrieving the calibration image and the reference spectra from a memory of a mobile computing device; and controlling a handheld spectroradiometer to transmit the non-calibration image to the mobile computing device.

Example 18

The method of Examples 16 or 17, further comprising retrieving the calibration image, the reference spectra, and the non-calibration image from a memory of a handheld spectroradiometer.

Example 19

The method of any of Examples 16-18, wherein the non-calibration image further includes spectral data regarding an object-of-interest, the method further comprising: detecting a characteristic of the object-of-interest by performing a spectral analysis on the spectral data.

Example 20

The method of Example 19, wherein the object-of-interest is a body of water, and wherein the characteristic that is detected is one or more characteristics selected from a group consisting of: a presence of blue-green algae, a clarity of the body of water, a concentration of chlorophyll, a concentration of dissolved organic carbon, and a concentration of suspended minerals.

The embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling with the spirit and scope of this disclosure.

It is believed that embodiments described herein and many of their attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

Thus, embodiments described herein provide, among other things, non-transitory computer-readable media, spectroradiometer systems, and methods for calibrating a spectroradiometer. Various features and advantages are set forth in the following claims.

What is claimed is:

1. A non-transitory computer-readable medium comprising instructions that, when executed by an electronic processor, cause the electronic processor to perform a set of operations comprising:

receiving spectral data regarding an object-of-interest that is captured by a handheld spectroradiometer;

detecting a characteristic of the object-of-interest by performing a spectral analysis on the spectral data that is received;

controlling a display to display the characteristic of the object-of-interest;

mapping each pixel in a calibration image to a wavelength;

averaging spectra of each pixel in the calibration image together;

determining a correction factor by comparing the spectra that is averaged together to reference spectra; and regularizing the spectral data regarding the object-of-interest by applying the correction factor that is determined.

2. The non-transitory computer-readable medium of claim 1, wherein the set of operations further includes retrieving the calibration image and the reference spectra from a memory; and controlling a handheld spectroradiometer to transmit the spectral data regarding the object-of-interest.

3. The non-transitory computer-readable medium of claim 1, wherein the object-of-interest is a body of water, and wherein the characteristic that is detected is one or more characteristics selected from a group consisting of:

a presence of blue-green algae, a clarity of the body of water, a concentration of chlorophyll, a concentration of dissolved organic carbon, and a concentration of suspended minerals.

4. A spectroradiometer system comprising:

a mobile computing device including
a memory,
a communication interface, and
an electronic processor communicatively connected to the memory and the communication interface, the electronic processor configured to receive spectral data regarding an object-of-interest, and
detect a characteristic of the object-of-interest by performing a spectral analysis on the spectral data that is received; and a handheld spectroradiometer including
an image sensor with a diffraction device,
a memory,
a communication interface, and
an electronic processor communicatively connected to the memory, the communication interface, and the image sensor with the diffraction device, the electronic processor configured to control the image sensor to capture the spectral data regarding the object-of-interest based on reflected light from the object-of-interest;

wherein the electronic processor of the mobile computing device is further configured to:

map each pixel in a calibration image to a wavelength;

average spectra of the each pixel in the calibration image together;

determine a correction factor by comparing the spectra that is averaged together to reference spectra, and regularize the spectral data regarding the object-of-interest by applying the correction factor that is determined.

5. The spectroradiometer system of claim 4, wherein the memory of the mobile computing device includes the calibration image and the reference spectra, and wherein the electronic processor of the mobile computing device is further configured to retrieve the calibration image and the reference spectra from the memory of the mobile computing device, and
receive the spectral data regarding the object-of-interest from the handheld spectroradiometer.

6. The spectroradiometer system of claim 4, wherein the communication interface of the mobile computing device and the communication interface of the handheld spectroradiometer are configured to wirelessly communicate with each other.

7. The spectroradiometer system of claim 4, wherein the communication interface of the mobile computing device and the communication interface of the handheld spectroradiometer are configured to communicate with each other via a wired connection.

8. The spectroradiometer system of claim 4, wherein the object-of-interest is a body of water, and wherein the characteristic that is detected is one or more characteristics selected from a group consisting of:
a presence of blue-green algae,
a clarity of the body of water,
a concentration of chlorophyll,
a concentration of dissolved organic carbon, and
a concentration of suspended minerals.

9. The spectroradiometer system of claim 4, wherein the handheld spectroradiometer is mounted to a housing structure of the mobile computing device, and wherein the mobile computing device is one selected from a group consisting of:
a smartphone,
a tablet,
a computer,
a shipborne control system,
a UAV control system,
an aircraft control system, and
a high resolution satellite control system.

10. A method for calibrating a spectroradiometer, the method comprising:
mapping each pixel in a calibration image to a wavelength;
averaging spectra of each pixel in the calibration image together;
determining a correction factor by comparing the spectra that is averaged together to reference spectra; and
regularizing spectra by applying the correction factor that is determined to spectra in a non-calibration image.

11. The method of claim 10, further comprising:
retrieving the calibration image and the reference spectra from a memory of a mobile computing device; and
controlling a handheld spectroradiometer to transmit the non-calibration image to the mobile computing device.

12. The method of claim 10, further comprising retrieving the calibration image, the reference spectra, and the non-calibration image from a memory of a handheld spectroradiometer.

13. The method of claim 10, wherein the non-calibration image further includes spectral data regarding an object-of-interest, the method further comprising:
detecting a characteristic of the object-of-interest by performing a spectral analysis on the spectral data.

14. The method of claim 13, wherein the object-of-interest is a body of water, and wherein the characteristic that is detected is one or more characteristics selected from a group consisting of:
a presence of blue-green algae,
a clarity of the body of water,
a concentration of chlorophyll,
a concentration of dissolved organic carbon, and
a concentration of suspended minerals.

15. A non-transitory computer-readable medium comprising instructions that, when executed by an electronic processor, cause the electronic processor to perform a set of operations comprising:
receiving spectral data regarding an object-of-interest that is captured by a handheld spectroradiometer;
detecting a characteristic of the object-of-interest by performing a spectral analysis on the spectral data that is received; and
controlling a display to display the characteristic of the object-of-interest;
wherein receiving the spectral data regarding the object-of-interest further includes:
controlling an image sensor of handheld spectroradiometer to capture the spectral data regarding the object-of-interest; and
wherein the set of operations further includes:
mapping each pixel in a calibration image to a wavelength;
averaging spectra of each pixel in the calibration image together;
determining a correction factor by comparing the spectra that is averaged together to reference spectra; and
regularizing the spectral data regarding the object-of-interest by applying the correction factor that is determined.

16. The non-transitory computer-readable medium of claim 15, wherein the set of operations further includes retrieving the calibration image and the reference spectra from a memory of a handheld spectroradiometer.

17. The non-transitory computer-readable medium of claim 15, wherein the object-of-interest is a body of water, and wherein the characteristic that is detected is one or more characteristics selected from a group consisting of:
a presence of blue-green algae,
a clarity of the body of water,
a concentration of chlorophyll,
a concentration of dissolved organic carbon, and
a concentration of suspended minerals.

18. A spectroradiometer system comprising:
a mobile computing device including:
a memory;
a communication interface; and
an electronic processor communicatively connected to the memory and the communication interface;
the electronic processor configured to:
receive spectral data regarding an object-of-interest; and
detect a characteristic of the object-of-interest by performing a spectral analysis on the spectral data that is received; and
a handheld spectroradiometer including:
an image sensor with a diffraction device;
a memory;
a communication interface; and
an electronic processor communicatively connected to the memory, the communication interface, and the image sensor with the diffraction device, the electronic processor configured to control the image sensor to capture the spectral data regarding the object-of-interest based on reflected light from the object-of-interest;
wherein the electronic processor of the handheld spectroradiometer is further configured to:
map each pixel in a calibration image to a wavelength;

average spectra of the each pixel in the calibration image together;
determine a correction factor by comparing the spectra that is averaged together to reference spectra; and
regularize the spectral data regarding the object-of-interest by applying the correction factor that is determined.

19. The spectroradiometer system of claim 18, wherein the memory of the handheld spectroradiometer includes the calibration image and the reference spectra, and wherein the electronic processor of the handheld spectroradiometer is further configured to retrieve the calibration image and the reference spectra from the memory of the handheld spectroradiometer.

20. The spectroradiometer system of claim 18, wherein the communication interface of the mobile computing device and the communication interface of the handheld spectroradiometer are configured to wirelessly communicate with each other.

21. The spectroradiometer system of claim 18, wherein the communication interface of the mobile computing device and the communication interface of the handheld spectroradiometer are configured to communicate with each other via a wired connection.

22. The spectroradiometer system of claim 18, wherein the object-of-interest is a body of water, and wherein the characteristic that is detected is one or more characteristics selected from a group consisting of:
a presence of blue-green algae;
a clarity of the body of water;
a concentration of chlorophyll;
a concentration of dissolved organic carbon; and
a concentration of suspended minerals.

23. The spectroradiometer system of claim 18, wherein the handheld spectroradiometer is mounted to a housing structure of the mobile computing device, and wherein the mobile computing device is one selected from a group consisting of:
a smartphone;
a tablet;
a computer;
a shipborne control system;
a UAV control system;
an aircraft control system; and
a high resolution satellite control system.

* * * * *